United States Patent [19]

Estes et al.

[11] 4,421,107
[45] Dec. 20, 1983

[54] SURGICAL RETRACTOR ELEMENTS AND ASSEMBLY

[76] Inventors: Roger Q. Estes; Jeffery S. B. Estes, both of W. 700 7th Ave., Spokane, Wash. 99204

[21] Appl. No.: 197,149

[22] Filed: Oct. 15, 1980

[51] Int. Cl.³ .............................................. A61B 17/02
[52] U.S. Cl. ....................................... 128/20; 128/346
[58] Field of Search ................. 128/20, 17, 346, 87 R, 128/303 R

[56] References Cited

U.S. PATENT DOCUMENTS

| 2,623,517 | 12/1952 | Barlow et al. | 128/20 |
| 2,893,378 | 7/1959 | Cooper | 128/20 |
| 3,038,468 | 6/1962 | Raeuchle | 128/20 |
| 3,040,739 | 6/1962 | Grieshaber | 128/20 |
| 3,384,078 | 5/1968 | Gauthier | 128/20 |
| 3,394,700 | 7/1968 | Yamamoto | 128/20 |
| 3,463,144 | 8/1969 | Hammond | 128/20 |
| 3,522,799 | 6/1970 | Gauthier | 128/20 |
| 3,749,088 | 7/1973 | Gauthier | 128/20 |
| 3,882,855 | 5/1975 | Schulte et al. | 128/20 |
| 3,965,890 | 6/1976 | Gauthier | 128/20 |
| 3,998,217 | 12/1976 | Trumbull et al. | 128/20 |
| 4,337,762 | 7/1982 | Gauthier | 128/20 |

FOREIGN PATENT DOCUMENTS

| 512190 | 4/1955 | Canada | 128/20 |
| 2230025 | 7/1978 | Fed. Rep. of Germany | 128/20 |

OTHER PUBLICATIONS

Fackler–"Extending the Usefulness of Self-Retaining Retractors" American Journal of Surgery, Jun. 1975; vol. 129, pp. 712–715.

Matles, et al–"Ein Hochfester, rontgenstrahlendurchlassiger Bauchrahmen aus kohlenstoffaserverstarktem Kuntstoff" Derchirurg 1978, pp. 253–254.

Dittmar & Penn Catalog–"Self-Retaining General Retractors".

Primary Examiner—Lee S. Cohen
Assistant Examiner—Angela D. Sykes
Attorney, Agent, or Firm—Wells, St. John & Roberts

[57] ABSTRACT

Surgical retractor elements and assemblies are described for holding open a surgical incision to expose the surgical area and to keep uninvolved tissues away from the surgical area without causing undue trauma to the engaged tissues. A self-retaining form includes a ring frame and a plurality of paddle assemblies angularly spaced about the ring for engaging and holding back uninvolved tissues. The paddle assemblies have arms that slide radially through a slot in the ring frame. Each of the retractor assemblies includes a paddle of a soft, resilient flexible material for flexing to prevent stress concentrations. The paddle members have a flexural modulus of elasticity between 1,000 psi and 75,000 psi. One form of paddle is provided to slidably fit over the existing blade of a hand-held retractor. Another form of assembly includes a soft, resilient paddle mounted to a hand-held handle frame. The handle includes two angularly offset gripping sections that can be comfortably gripped and held by an assistant for long periods of time.

41 Claims, 19 Drawing Figures

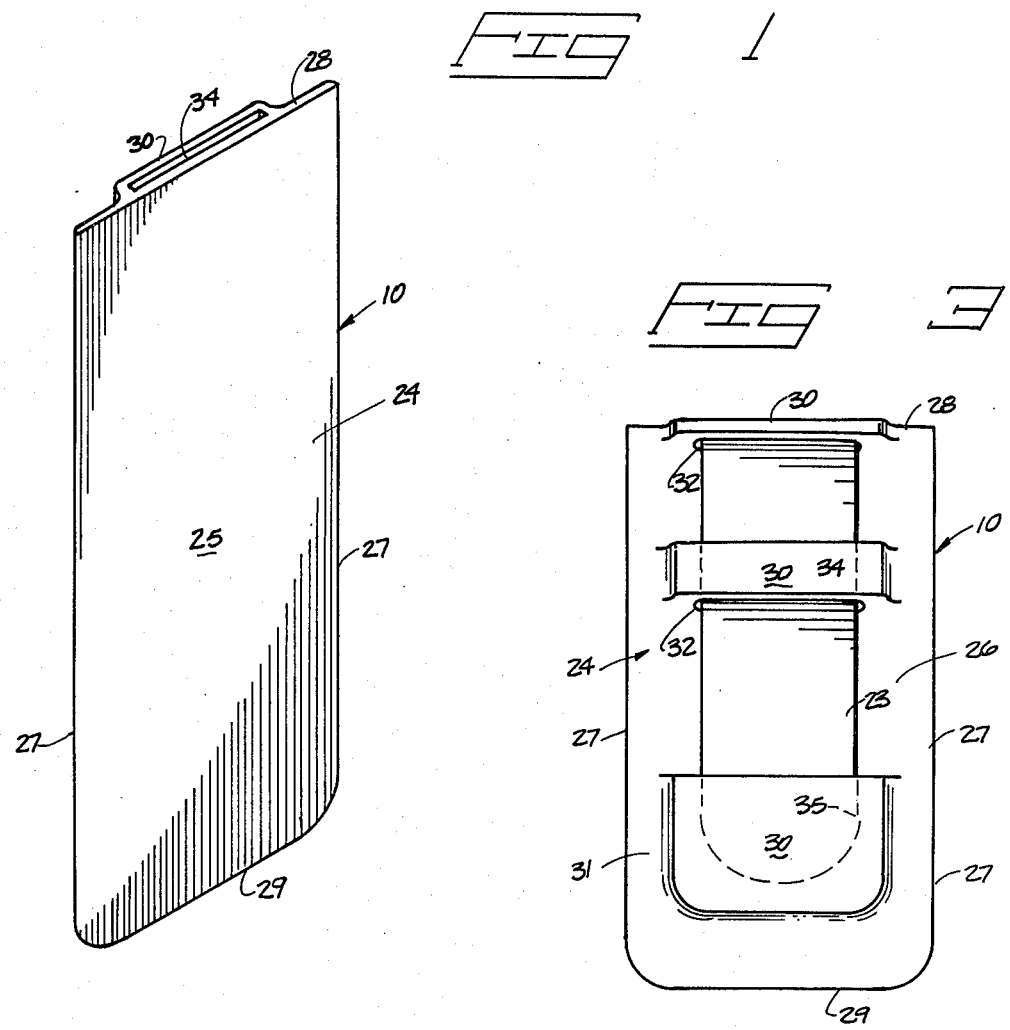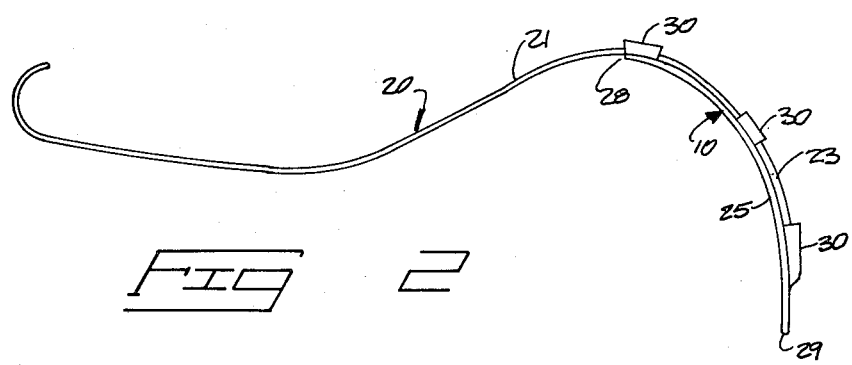

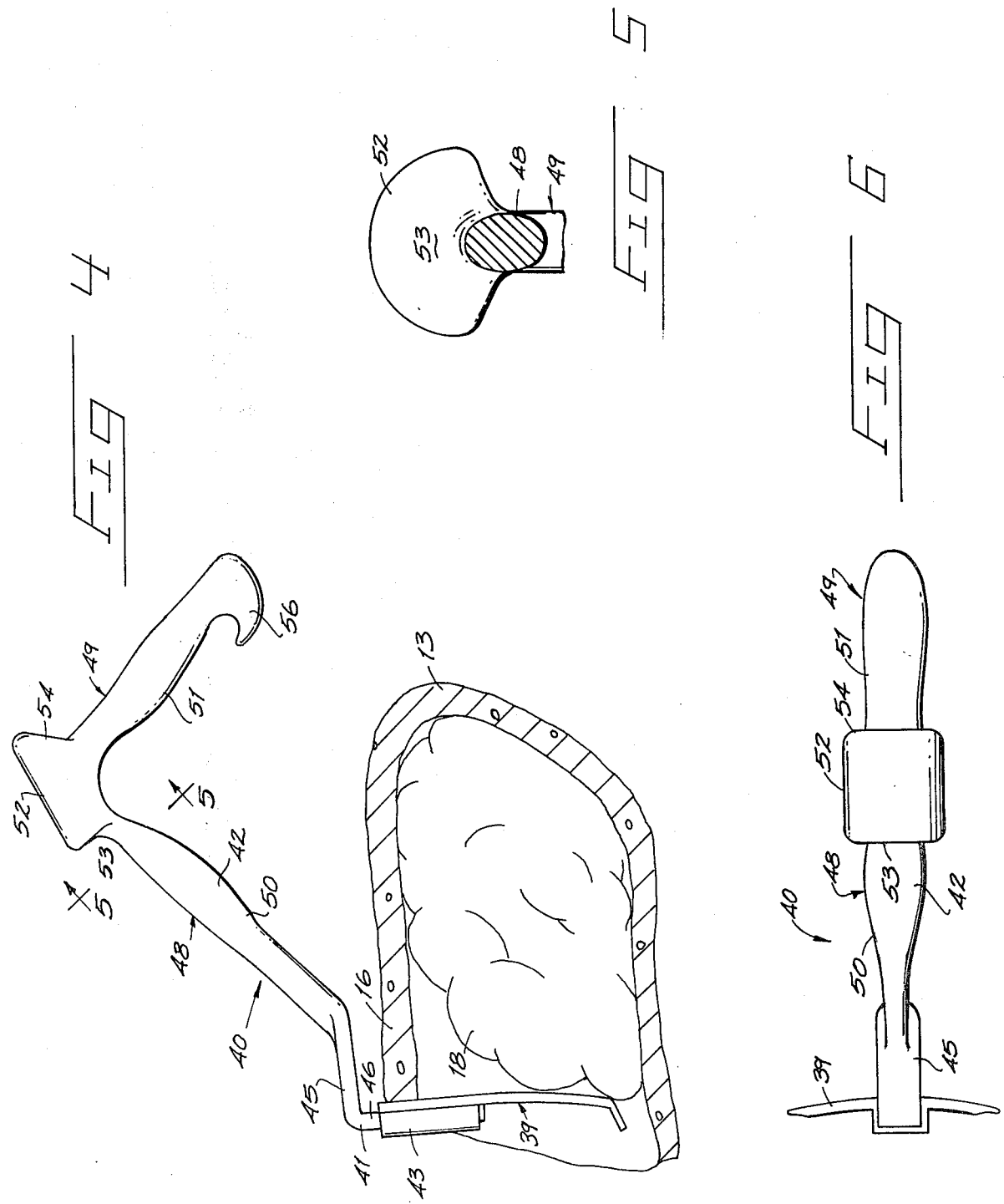

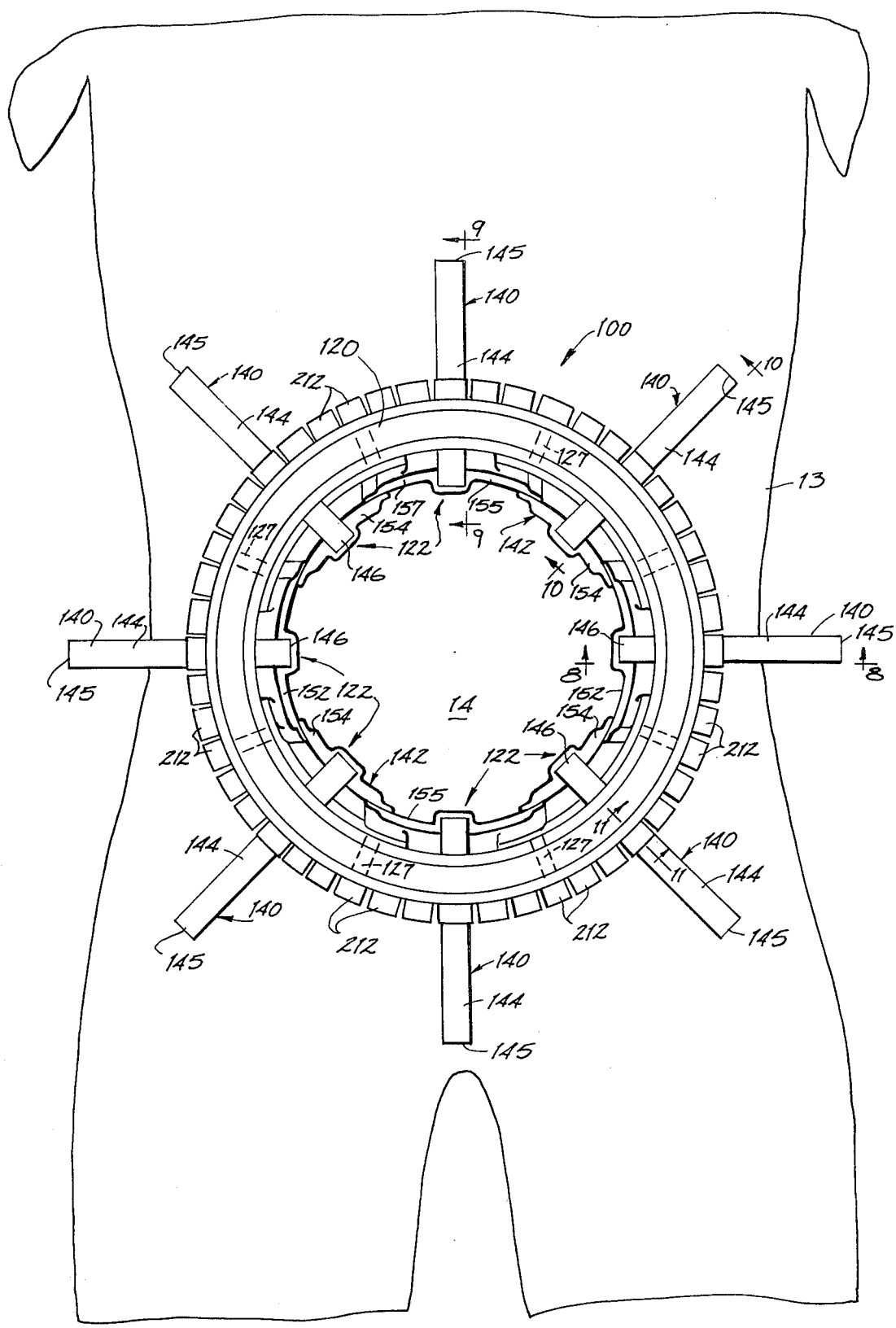

SURGICAL RETRACTOR ELEMENTS AND ASSEMBLY

TECHNICAL FIELD

This invention relates to surgical devices and more particularly to surgical retractor paddles and associated elements used to hold an incision open and to hold back (retract) adjacent tissues (e.g.: bowel) allowing exposure of organ(s) requiring surgery.

BACKGROUND

Over the years numerous types of surgical retractors have been developed to hold an incision open during the surgical operation. By holding uninvolved tissue (including skin, fat, muscle, nerves and organs) behind various types of blades or paddles, a cavity is produced in which a surgical procedure can be executed with the required good vision for precise technique. Retractors are also used to hold the border of the incision stable.

Many of the retractors have included a ring or circular element. Several angularly positioned paddle shaped retractor elements mount to the ring element and project into the incision to hold the incision open and to barricade the invasion of uninvolved tissues into the surgical cavity.

Several retractor arms have been constructed that allow adjustment of the opening of the incision. Such arms may be adjusted by tightening or loosening some type of screw or clamp elements that are fixed to the ring portion. Examples of such retractors are illustrated in U.S. Pat. Nos. 2,623,517; 2,893,378; 3,040,739; and 3,384,078. Several of the surgical retractors have been of the self-retaining type. Included is a paddle or hook with a lip that extends outward underneath the body tissues. The paddle maintains the retractor in position and prevents the retractor from migrating during the surgical process. Examples of such paddle elements are illustrated in U.S. Pat. Nos. 2,623,517 and 3,394,700.

The typical retractor paddle is formed of a stainless steel or reinforced plastic material that has a curved surface for engaging the body tissues. An example of such a blade or paddle is illustrated in U.S. Pat. No. 3,384,078.

The devices described above have been known to press upon nerves, producing damage and paralysis. Additionally, the surgeon must be careful when expanding the incision not to trap bowel or body organs beneath the edges of the paddles or hooks. Otherwise the tissue might be damaged. Additionally, the paddles are rigid and unforgiving, placing substantial stress concentration on the body tissues. The potential for trauma is thereby increased and may increase the recovery time for the patient. In the United States millions of surgeries are performed each year utilizing surgical retractors. A savings of one day of recovery time would represent a very significant decrease in the cost of hospitalization and patient discomfort.

Additionally, absorbent cotton materials (called sponges) are generally used in conjunction with surgical retractors to pack away uninvolved tissues so as not to impede the progress of the operation. Sponges can contribute to tissue dehydration. Sponges are occasionally left in the abdomen after the surgery is completed and the incision closed. Sponge retention often causes severe complications. Furthermore, sponges are carriers of a variable degree of lint. Lint alone, when retained in the abdominal cavity can cause irritation, inflammation, and adhesions which may result in prolonged discomfort, or severe complications.

One of the principal objects of this invention is to provide surgical retractor elements that are capable of engaging and holding back the uninvolved body tissues from the site or locus of the operation while minimizing stress concentrations on the abdominal wall and materially reducing the potential for trauma to tissues held out of the surgical cavity by the retractor paddle.

A further object of this invention is to provide stable surgical retractor elements that are capable of being readily manipulated and adjusted by the surgeon or an assistant.

A further object of this invention is to provide versatile surgical retractor elements which permit a reduction in members of the surgical team. Additionally, fewer assistants may be required which reduces the surgical costs.

A further object of this invention is to provide surgical retractor elements that are capable of significantly reducing body tissue trauma and thereby reduce recovery and hospitalization time.

A further advantage of this invention is to provide surgical retractor elements that are highly adjustable, enabling the system to be utilized on a wide variety of patients having a wide diversity in flesh thickness and body cavity depth.

A still further object of this invention is to provide surgical retractor elements that reduce the need for sponges.

These and other objects and advantages of this invention will become apparent upon reading the following detailed description.

BRIEF DESCRIPTION OF THE DRAWINGS

The present invention is illustrated in the accompanying drawings, in which:

FIG. 1 is a pictorial view of a paddle for mounting to an existing form of retractor;

FIG. 2 is a side elevation of the paddle shown in FIG. 1 only mounted to an existing form of hand-held retractor;

FIG. 3 is a rear view of the paddle and retractor shown in FIG. 2;

FIG. 4 is a side view of a hand-held form of the retractor assembly;

FIG. 5 is a cross-sectional fragmentary detail view of a portion of the assembly shown in FIG. 4 taken along line 5—5 in FIG. 4;

FIG. 6 is a top plan view of the assembly shown in FIG. 4;

FIG. 7 is a plan view of a self-retaining surgical retractor showing present retractor elements and a retractor assembly utilized in conjunction with abdominal surgery on a patient;

DETAILED DESCRIPTION OF PREFERRED EMBODIMENTS

Figure 8:
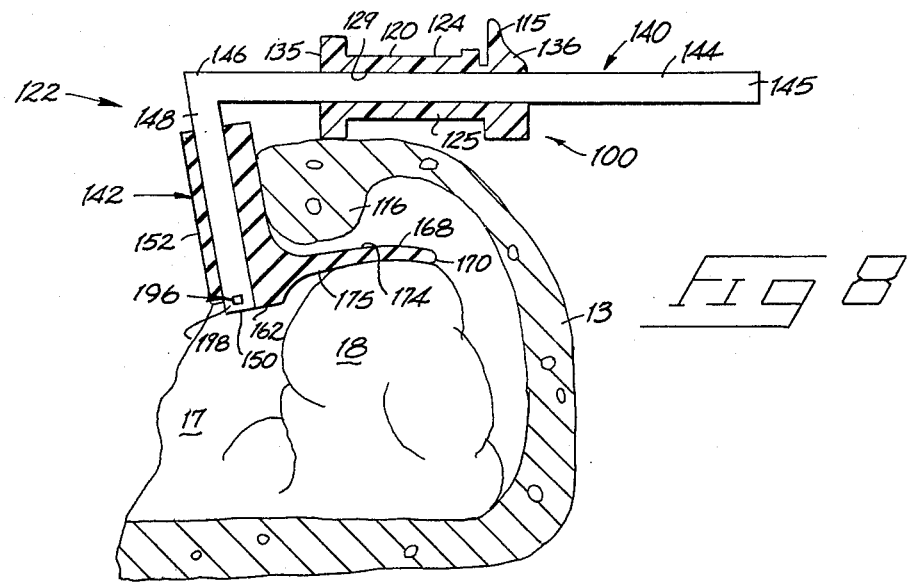
FIG. 8 is a vertical cross-sectional schematic view taken along line 8—8 in FIG. 7 illustrating a lateral paddle assembly.

Several forms of the present surgical retractor elements and assemblies are shown in the accompanying drawings. Specifically, FIGS. 1 through 3 show one form of the present retractor paddle that is adapted to be mounted on a conventional hand-held retractor. FIGS. 4 through 6 show a form of the present hand-held retractor assembly, including a hand-held frame and paddle. A form of the present assembly is also shown in conjunction with a self-retaining retractor assembly in FIGS. 7 through 19.

All forms of the present retractor elements and assemblies are intended for surgical use on an animal or human body 13 (FIGS. 4, 7 and 8 through 10) to hold a surgical incision open. The primary object of the retractor elements and assemblies is to hold the incision open, allowing a surgeon to effectively and efficiently perform a surgical procedure within a surgical area 14. As shown in FIG. 7, the incision is made in the abdominal area of the body 13. The present retractor elements and assemblies operate to hold back body "tissues" adjacent the incision. For purposes of this disclosure, the purposely generalized term "tissues" will be taken to include body wall flesh 16 (including sking, fat, muscle, and nerve tissues) and the body viscera 18.

One form of a retractor paddle element of the present invention is shown particularly in FIGS. 1 through 3 at 10. This particular element of the present invention is adapted for mounting to conventional hand-held retractors such as that shown at 20 in FIG. 2.

Conventional hand-held retractors 20 may be formed either of an integral handle 21 and blade 23 as shown, or can include a solid cast handle and a stiff wire blade (not shown). In surgery, the "blade" is inserted into an incision and is positioned adjacent tissues desired to be held away from the surgical area 14. The task of holding the blade in place and providing sufficient force against the blade to hold the uninvolved tissues away from the area 14 is typically assigned to an assistant. Often several such retractors are used, along with an equal number of assistants. Also, such hand-held retractors are not uncommonly used in conjuction with self-retaining retractors for specific, localized applications within the surgical area.

The illustrated paddle 10 includes a body 24 formed entirely of a soft, resilient, non-metallic, non-absorbent material such as urethane, vinyl, rubber or other appropriate material. The material is scissile, allowing the surgeon to quickly and easily cut the paddle into any size or configuration desired.

The material used for the paddle 10 and for the other paddle forms shown and described below is soft and flexible with an operable flexural modulus of elasticity range between 1,000 psi and 75,000 psi. Preferably, however, the range is between 2,000 psi and 20,000 psi. The operable "softness" durometer range of the material is softer than D-69 Shore but harder than A-20 Shore. The preferable range, however, is softer than A-99 Shore and harder than A-60 Shore.

The material is thus sufficiently soft and resilient to allow the paddle body 24 to bend into an arc, evenly distributing forces to the engaged tissue without producing stress concentrations that would otherwise be likely to damage or traumatize the affected tissues.

The paddle body 24 includes a front face 25 that is adapted to engage body tissues including the body wall flesh 16 and viscera 18. The body 24 also has a back face 26 that is adapted to face inwardly toward the surgical area 14. The faces 25 and 26 extend to peripheral side edges 27. The edges 27 are preferably upright and joined by a peripheral top edge 28 and an opposed bottom edge 29.

The paddle body 24 includes a thickness dimension between the front and back faces that decreases from the central portion toward side edges 27. The thickness dimension preferably decreases toward the bottom edge 29. The decreasing paddle thickness feature, coupled with the material characteristics described above, allow the body 24 to deflect resiliently into two dimensional arcs between edges 27 and edges 28 and 29 in response to forces applied thereto.

The body 24 includes one or more thick central sections 30 and thin peripheral skirt sections 31 leading to the edges 27 and 29. The thin peripheral sections are scissile, allowing the surgeon to cut the paddle to any desired shape or size according to need.

The thick central sections 30 include means at 32 along the back face of the body adapted to mount a retractor frame, such as the retractor blade 23 of FIG. 2. A vertical slot 34 is formed lengthwise through the thick central sections 30 of a shape that is complementary to the cross-sectional configuration of the blade 23. The blade 23 is thus slidably received through the aligned slots 34. The resilient material conforms intimately to the curvature of the blade, with the peripheral sections 31 at the sides projecting laterally of the blade sides and the skirt section 31 at the bottom projects downwardly beyond the paddle end. The blade end is received in a bottom closed pocket 35 of the means 32. The central portions 30 of the paddle will conform to and are reinforced by the blade 23. The peripheral sections 31, however, are allowed to flex resiliently about the retractor blade. The thin sections 31 are able to bend sharply about short radii and at angles approaching 90° to the normal planar orientation of the faces. This flexural "give" eliminates stress concentrations that would otherwise occur at the rigid edges of the conventional blade 23.

It is understood that the retractor 20 shown herein is merely one of many conventional forms currently in use. It should be understood, however, that the present paddle structure is sufficiently resilient and pliable to fit over many blade configurations. Furthermore, the paddle 10 can also be produced with varying shape and size slots 34 to conform to virtually any retractor blade structure.

FIGS. 4 through 19 show modified forms of the paddle described above for use as an element of (1) a novel hand-held retractor assembly 40 (FIGS. 4 through 6) and (2) a novel self-retaining retractor assembly 100 (FIGS. 7 through 19). In such embodiments, the paddles are preferably included as elements of retractor assemblies 40 or 100. The paddles 10 themselves, however, are adjustably mounted to respective mounting means for vertical adjustment as will be described below.

The hand-held retractor assembly 40 basically includes an integral paddle mounting arm 41 and hand grip handle 42. Assembly 40 allows a surgical assistant to comfortably hold an incision open for extended periods of time without the usual accompanying fatigue so often associated with conventional hand-held retractors.

The paddle 39 of this embodiment is nearly identical with the form shown in FIGS. 1 through 3 with the exception that a single elongated central thickened section 43 may be provided in place of the several sections 30 of the FIG. 1 through 3 version.

The mounting arm 41 (FIG. 4) includes a horizontal section 45 and an upright section 46 for mounting the paddle 39. The two sections are shown at right angles. However, it is understood that other angular relationships (acute or obtuse) might be utilized as well.

Figure 13:
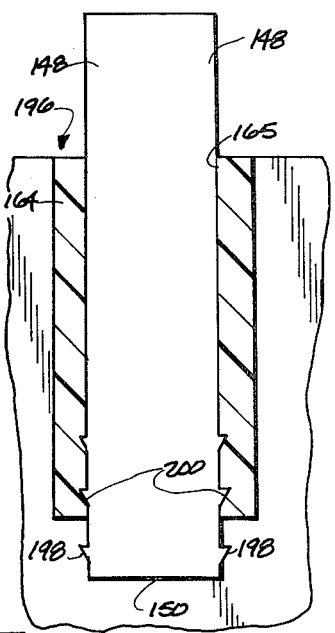
FIG. 13 is a vertical cross-sectional view taken along line 13—13 in FIG. 9 illustrating a vertical adjustment mechanism for adjusting the paddles with respect to the patient.

The upright section 46 may include an adjustable mounting means (not shown) that is similar to that shown in detail by FIG. 13 and described below for the self-retaining retractor 100. Section 46 mounts the paddle 39 to the mounting arm 41 for vertical adjustment thereon. Effective penetration of the paddle into the body cavity can thus be varied according to need. More detailed description of a similar adjusting means will be given in conjunction with the description of the self-retaining retractor 100 below.

The hand grip handle 42 includes a first handle section 48 leading up and outwardly from the arm 41. A second handle section 49 projects downward from the section 48. It is preferable that the first handle section 48 form an obtuse angle with the horizontal section 45 of paddle mounting arm 41. It is also preferable that the second handle section 49 be substantially perpendicular to the first section 48.

The first handle section 48 provides a hand grip surface 50. The surface 50 facilitates a comfortable grip by one of an assistant's hands. The second handle member likewise has a hand grip surface 51 grasped by the other of the assistant's hands. The perpendicular relationship of the grip surfaces to each other and to the arm 41 allows orientation for superior mechanical advantage of the assistant's hands to assure a firm grip on the retractor and to lessen fatigue.

A hand stop 52 is provided between the first and second handle sections 48, 49 to abut with the hand gripping the first section. The stop 52 is shaped along the surface 53, facing section 48, to conform to the side of a user's hand. FIG. 5 shows the enlarged area of the abutment surface 53.

A side of stop 52 opposite surface 53 includes a thumb brace surface 54. The thumb brace surface 54 faces the second section 49 to provide a surface against which a user's thumb may comfortably rest. The surface 54 is preferably concave to conform to the surface of the thumb (FIG. 6).

Opposite the thumb brace surface 54 and at a remote end of the handle is another hand stop 56 (FIG. 4). The side of the user's other hand bears against the stop 56. The stop 56 effectively prevents the hand from slipping off the handle surface 51. Consequently, the assistant's hand against the surface 51 may be rather relaxed. The stop 56 is hook shaped and extends down and inward to engage the side of the user's hand.

The self-retaining form of the surgical retractor assembly 100 (FIGS. 7-12) includes a circumscribing or annular frame or ring member 120 that is made of a rather rigid material for circumscribing the surgical area 14. The frame preferably has a modulus of elasticity greater than 300,000 psi.

The retractor 100 further includes a plurality of paddle assemblies 122 that are operably mounted to the ring member 120. The assemblies 122 are angularly spaced about the surgical area 14 for engaging uninvolved tissues. The paddle assemblies 122 serve to maintain the incision open without the aid of an assistant and to facilitate surgical operations without interference from uninvolved tissues.

Preferably, the ring member 120 is made as a unitary member with an upper ring plate 124 (FIGS. 8-12) and a lower ring plate 125 vertically separated by angularly spaced ribs 127 shown by dotted line in FIG. 7. The ribs 127 are preferably quite narrow so that an annular slot 129 (FIGS. 8-10) of substantially 360° is formed between the upper plate 124 and the lower plate 125. The ribs 127 provide rigid support between the plates 124 and 125. The annular slot 129 extends from an inner face 135 (FIGS. 8-10) of the ring member 120 to an outer face 136. The annular slot 129 is capable of receiving a plurality of paddle assemblies 122.

Each of the paddle assemblies 122 includes an arm frame member 140 and a paddle 142 (FIGS. 7-10). The arm frame member 140 includes a horizontal section 144 that extends radially through the annular slot 129 in a close sliding fit between the top and bottom ring members 124, 125. In a preferred embodiment, the horizontal section 144 has a substantially rectangular cross section so that the paddle assemblies 122 will not rotate about the horizontal section 144.

Each horizontal section 144 extends from an outer end 145 to an inner end 146. The inner end 146 forms part of a bend that is integral with an upright section 148. The section 148 extends downward to a terminal lower end 150 (FIGS. 8-10 and 13). The bend illustrated forms an acute angle between the horizontal section 144 and the upright section 148. Preferably the acute angle is between 75° and 85° so the paddle 142 will extend downward and outward with respect to the surgical area 14. It is noted that though the above angular range is preferred, in some operations other angles are envisioned, including obtuse angles.

A preferred retractor 100 has three general types of paddles. Such paddles 142 include lateral paddle member 152 (FIGS. 7, 8, 14 and 15) that are positioned laterally from the axis of the incision or at the 90° and 270° positions with respect to the axis of the body when abdominal surgery is being performed as illustrated in FIG. 7. The paddles 142 may include polar paddle members 155 (FIGS. 7, 9, 16 and 17) that may be positioned perpendicularly to the lateral paddle members 152. Additionally, paddles 142 may include lap paddle members 154 (FIGS. 7, 10, 18 and 19) that are interposed between the lateral members 152 and the polar members 155 depending upon the type of operation. When a rather large incision is made in the abdominal area the lap paddle members 154 may be positioned intermediate the lateral members 152 and the polar members 155 at the 45° position, the 135° position, the 225° position, ad the 315° position. It should be noted that when all of the paddle members 152, 154 and 155 are utilized, a substantially 360° enclosure is formed which may be referred to as a "coffer dam" to minimize the intrusion of body viscera 18 into the surgical area. Consequently, the need for sponges is greatly reduced and possibly eliminated.

It is preferred that each of the paddles 142, like paddles 10 and 39 are formed of a non-metallic soft, resilient material that is scissile and capable of being deformed or flexed to conform to the tissues about the periphery of the incision. The paddles 142 are preferably interchangeable with the paddle members 39 shown in FIGS. 4–6. The paddles 10, 39 and 142 have the same physical material properties. The paddle members will thus conform and flexibly deflect in response to the contours and tensions of the body tissues. The paddle material will conform in response to the reactive forces placed upon the paddles as the paddle assemblies 122 are moved radially outward to spread the incision open and to maintain the surgical area unobstructed.

Each of the paddles 142 includes a body 157 (FIGS. 7, 8–10, 14, 16 and 18) having a front face 156 that is adapted to engage the body wall flesh 16 and vascera 18. The body 157 has a back face 158 that faces the surgical area 14. The front face 156 and the back face 158 extend outwardly to peripheral side edges 160, a peripheral top edge 161 and a peripheral bottom edge 162.

The paddle members 142 have a decreasing thickness from the central portion towards the side edges 160. The paddle members 142 will thus deflect in a curved arc in response to the reactive forces placed on the front face 156. During use the front face 156 forms a substantial arc between the peripheral side edges 160 with the pressures being distributed over the front face 156 to minimize stress concentrations. The peripheral side edges 160 are rather thin and quite pliable to enable the edges 160 to progressively bend in arcs having small radii of curvature to minimize and prevent stress concentrates along the peripheral edges 160.

The back face 158 includes an enlarged section 164 that has a vertical slot 165 formed therein for slidably receiving the vertical section 148 of the arm member 140.

Each of the lateral paddle members 152 includes a rather thick central section 166 and thin peripheral sections 167 leading to the peripheral side edges 160.

The lateral paddle members 152 include a retaining projection 168 that extends outward from the front face 156 terminating in a leading edge 170. The retaining projections 168 include side edges 172 and 173 that extend rearward from the leading edge to the central section 166. The retaining projection 168 has a top surface 174 and a bottom surface 175. The retaining projection 168 is designed to extend outward from the incision into the body cavity intermediate the body wall flesh 16 and the body viscera 18. The top surface 174 is intended to engage the body wall flesh 16. The retaining projection 168 holds the retractor 10 within the incision and prevents the retractor 10 from being ejected or dislodged from the incision. The lateral paddle 152 includes a very minimal skirt 176 that extends downward a slight distance from the retaining projection 168.

The lateral paddle members 152 are principally designed to maintain the incision in an open position against the tension of the body wall flesh with the retaining projection 168 securing the retractor 100 within the incision. In response to the tension of the tissues the front face 156 of the lateral member 152 forms an arc against the body wall flesh 16 as illustrated in FIG. 7 to eliminate points of stress concentration. The degree of arc is dependent upon the width of retraction relative to incision length. Frequently, the lateral paddle members of conventional retractors press against nerve elements such as the femoral cutaneous nerves and it is very important that undue stress concentrations be minimized to prevent nerve damage. The lateral member 152 illustrated in FIG. 14 has a radius 178 between the central section 166 and the peripheral section 167 so that the peripheral side sections 167 may readily bend in arcs to prevent sharp stress concentrations adjacent the edges and thus avoid nerve damage or damage to other adjacent tissues.

Figure 16:
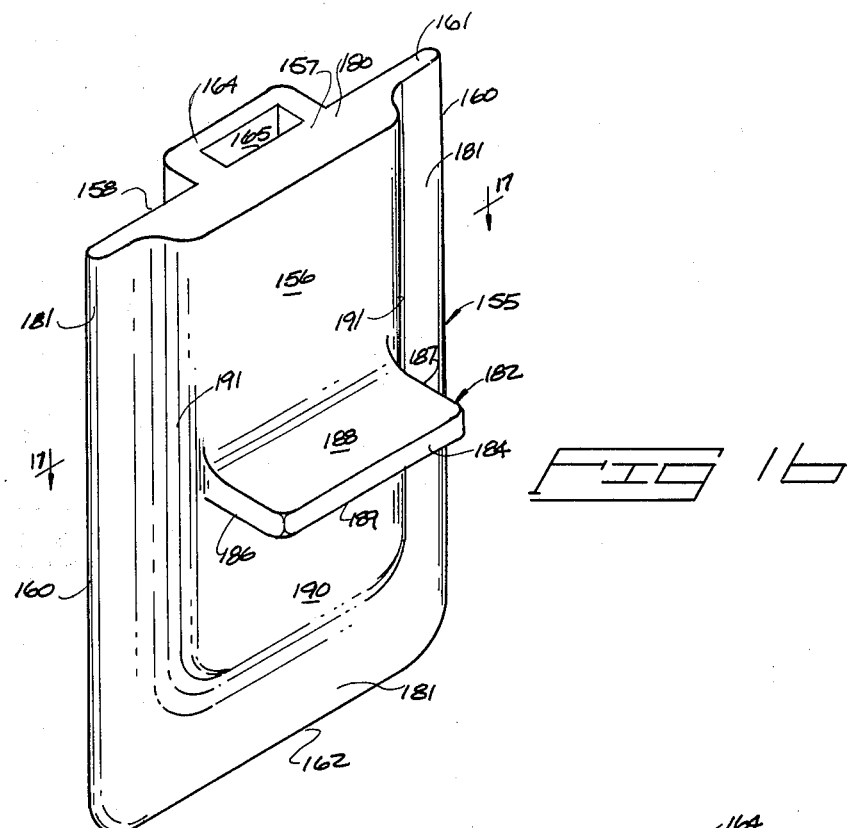
FIG. 16 is an isometric view of a polar paddle member illustrated in FIG. 9.
Figure 17:
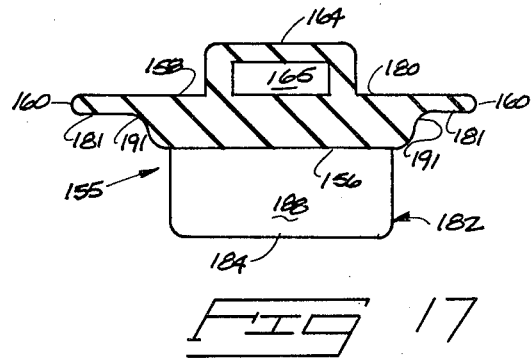
FIG. 17 is a horizontal cross-sectional view taken along line 17—17 in FIG. 16.

The polar paddle members 155 (FIGS. 16 and 17) include a central section 180 with a peripheral section 181 extending outward to the peripheral side edges 160 and the peripheral bottom edge 162 as illustrated in FIGS. 16 and 17.

Figure 9:
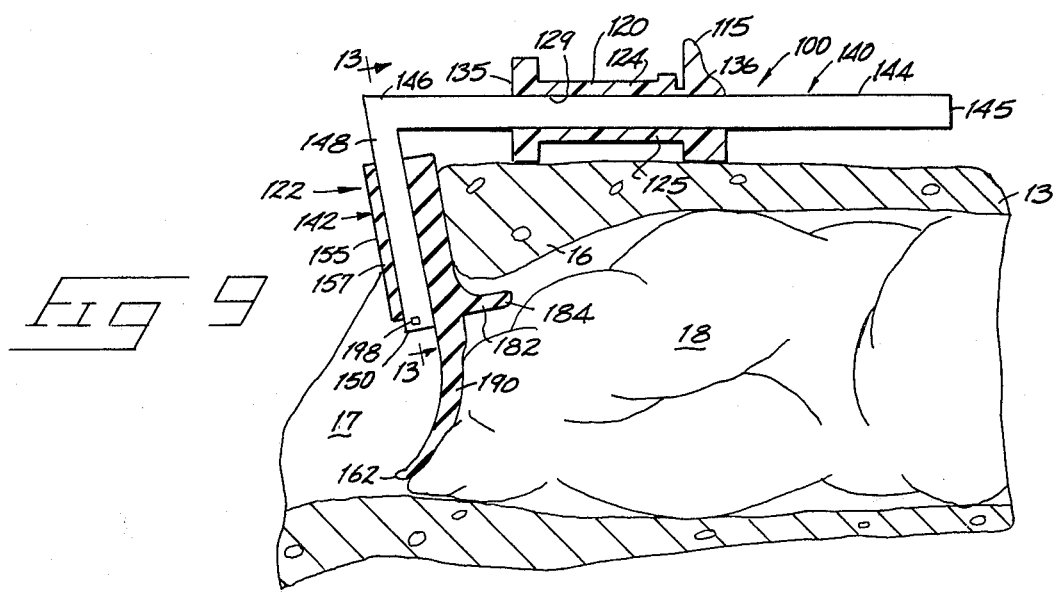
FIG. 9 is a vertical cross-sectional schematic view taken along line 9—9 in FIG. 7 illustrating a polar paddle assembly.
Figure 10:
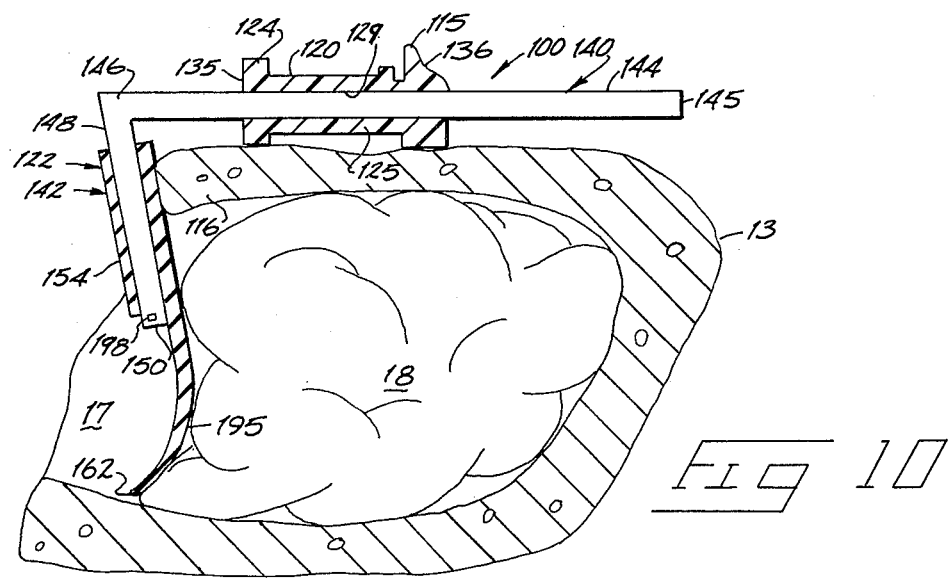
FIG. 10 is a vertical cross-sectional schematic view taken along line 10—10 in FIG. 7 illustrating a lap paddle assembly.
Figure 11:
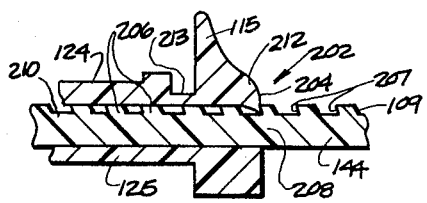
FIG. 11 is a vertical cross-sectional view taken along line 11—11 in FIG. 7 illustrating a one-directional adjustment locking mechanism.
Figure 12:
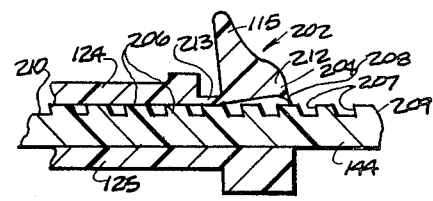
FIG. 12 is a view similar to FIG. 11 except showing the release of the locking mechanism.
Figure 14:
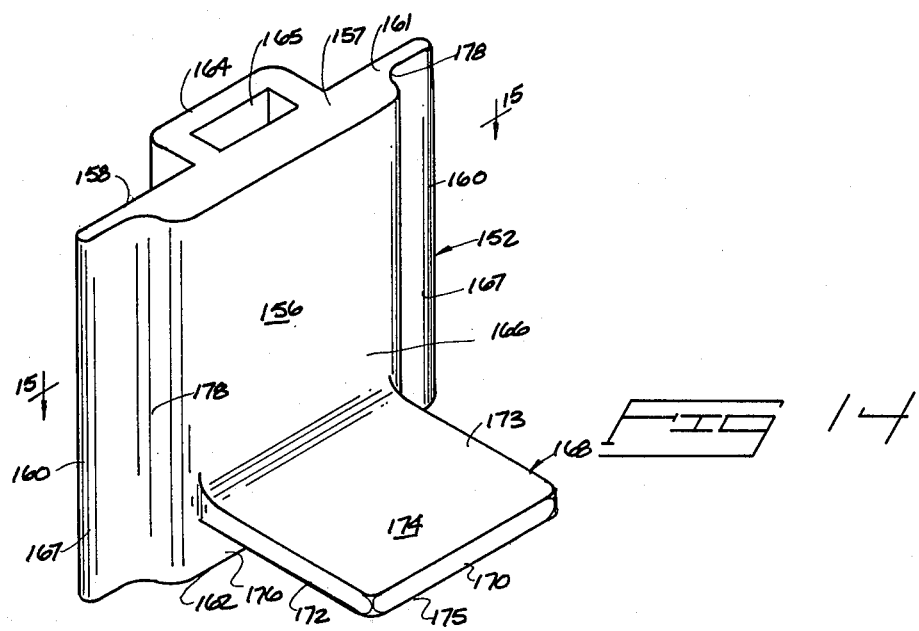
FIG. 14 is an isometric view of a lateral paddle member illustrated in FIG. 8.
Figure 15:
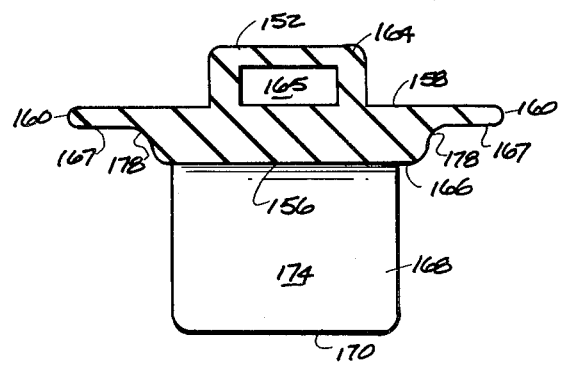
FIG. 15 is a horizontal cross-sectional view taken along line 15—15 in FIG. 14.

The polar paddle members 155 include a retaining projection 182 that extends outward from the central section 180 to a leading edge 184. Preferably, the retaining projection 182 is considerably shorter than the retaining projection 168. The retaining projection 182 has side edges 186 and 187 extending rearward from the leading edge to the central section 180 forming a top surface 188 and a bottom surface 189. The top surface 188 is intended to fit immediately underneath the body wall flesh 16 as illustrated in FIG. 9.

The polar paddle members 155 each include a skirt section 190 (FIGS. 9 and 16) that extends downwardly a substantial distance from the projection 182 for bearing against the body viscera to hold the organs from the surgical area 14. As illustrated in FIGS. 16 and 17, the polar paddle members 155 each have a radius 191 formed in the front face 156 between the central section 180 and the peripheral section 181. The radius 191 substantially decreases the thickness of the polar paddle members 155 adjacent the peripheral side edges 160 and the bottom edges 162. It should be noted that the peripheral sections 181 adjacent the bottom edges 162 are capable of bending at least 90° without breaking so that the bottom edges 162 do not press dangerously against any nerve, vein, artery, ureter, or other body tissue elements. This feature is very important in preventing nerve and tissue damage, blood clots, arterial occlusion, or kidney obstruction via the ureteral drainage conduit.

Figure 18:
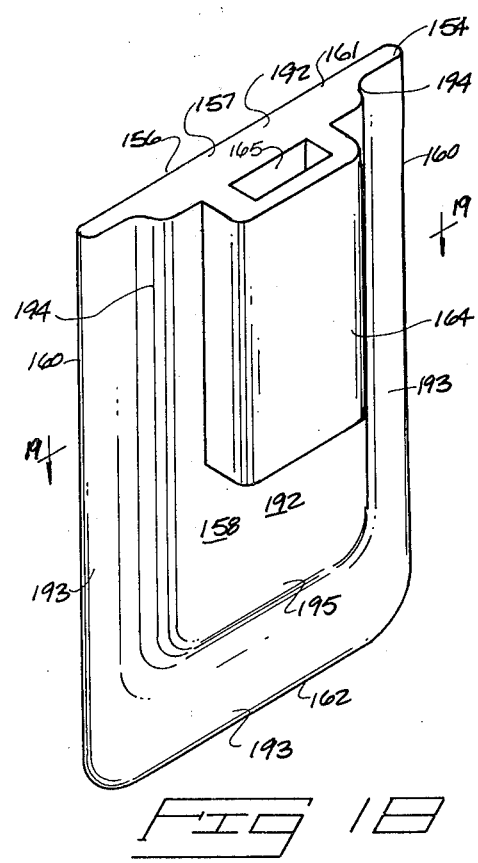
FIG. 18 is an isometric view of a lap paddle member illustrated in FIG. 10.
Figure 19:
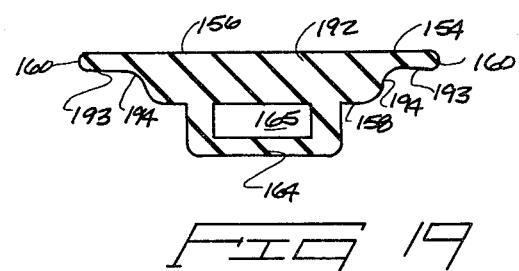
FIG. 19 is a cross-sectional view taken along line 19—19 in FIG. 18.

Each of the lap paddle members 154, illustrated in FIGS. 18 and 19, includes a central section 192 and a peripheral section 193 extending outward from the central section to the peripheral side edges 160 and bottom edge 162. Preferably the lap paddle members 154 are without any retaining projections and are principally designed to interlace between the lateral paddle members 152 and the polar paddle members 155 to engage and maintain the body viscera 18 from the surgical area 14. Each member 154 has a skirt 195 that extends downward a substantial distance into the body cavity to provide a barrier to the body viscera. A radius 194 is formed on the back face 158 of each lap paddle member 154 so that the peripheral side edges 160 thereof may overlap the adjacent peripheral side edges of the adjacent lateral paddle member 152 and polar paddle member 155 as illustrated in FIG. 7. The peripheral sections 167, 181 and 193 substantially overlap and form a sliding seal to reduce the exposed tissue surface area and resulting dehydration.

It should be noted that not all operations will require the use of the lap paddle members 154. However, they are quite useful, as are the other paddle forms, particularly as a substitute for sponges. They help prevent the loss of sponges within the body cavity and complications from lint deposition. Additionally, the paddles do not absorb body liquids (as do sponges), but leave the tissues in a more natural state with less dehydration. Such attributes provide for quicker patient recovery.

Each of the paddle assemblies 122 (and the hand-held retractor 40 described above) includes a vertical adjusting means 196 (FIG. 13) for vertically adjusting the paddle members 142 with respect to the arm members 140. Such a feature is illustrated in FIG. 13. The vertical adjusting means 196 includes rigid detent projections 198 formed on side edges of the vertical arm sections 148. Complementary series of recesses 200, formed in the vertical slots 165, enable the detent projections 198 to be received therein. Together they secure the paddle member 142 at a variety of desired elevations with respect to the horizontal arm sections 144. As illustrated in FIG. 13, the detent projections 198 extend below the enlarged sections 164 when the paddle member is located in uppermost position. The paddle assemblies 122, being two separate pieces, 142 and 140, allow the use of different length paddle members 142 providing additional vertical adjustment.

Each of the paddle assemblies 122 further includes radial adjustment means 202 (FIGS. 11 and 12) for enabling the paddle assemblies 122 to be quickly and easily radially adjusted with respect to the ring member 120. Preferably the radial adjustment means 202 includes a releasable one-directional locking means 204 that operatively interconnects the horizontal section 144 of the arm member 140 and the ring member 120. The locking means 204 preferably includes a series of ratchet teeth 206 formed in the upper surface of the horizontal section 144 adjacent to the outer end 145. Each of the ratchet teeth 206 includes an abutment surface 207 that is preferably inclined inward toward the inner end 146, forming an acute angle of approximately 85° with the horizontal section 144 of the arm member 140 and an inclined or ramp surface 209 that faces outward towards the outer end 145. A wide groove 210 is formed between the teeth 206. The wide groove 210 allows pivotal movement of the arm assemblies 122. The grooves 210 and the teeth 206 are preferably formed in arcs with respect to the center of the ring member 120 so that the arm members may slide circumferentially without releasing the locking means 204.

The locking means 204 further includes a plurality of biased pawls 212 (FIGS. 7, 11 and 12) that are positioned about the outer face 136 of the ring member 120. The biased pawls 212 are adjacent to each other and interconnected to the main portion of the upper ring plate 124 through a flexible web section 213. The web section 213 biases the pawls 212 downwardly to engage the teeth 206. The pawls 212 and the teeth 206 are designed so that the paddle assemblies 122 may be moved outwardly very easily be merely applying a radial force on the paddle assemblies 122 causing the horizontal section 144 to slide outward in the annular slot 129. The pawls 212 ride up the inclined surfaces 209 and then fall downwardly into the grooves 210 immediately adjacent the abutment surfaces 207. The pawls 212 have contact surfaces 208 that engage the abutment surface 207. Contact surfaces 208 are formed at acute angles of approximately 85° in relation to the lower surface of the upper ring plate 124. Such angled faces 208 mate with the angled abutment faces 207, enhancing the security of the locking means 204. When the desired position is reached the pawls engage themselves and the mating surfaces prevent the paddle assemblies 122 from moving radially inward unless the locking means 204 is intentionally released.

It should be noted that the biased pawls 212 are sufficiently close to each other to enable an arm 140 to be moved circumferentially about the center of the ring member 120 from one pawl 212 to an adjacent one without releasing the arm 140 or enabling the arm 140 to move inwardly. Such a feature provides a great deal of versatility and enables a surgeon or his assistant to readily adapt the angular positions of the paddle assemblies 122 to a particular circumstance and portion of the body. This can be done without having to first release the paddle assembly 122, move the paddle assemblies and then reset the locking means.

It should be particularly noted with respect to FIG. 7 that the paddle members 142 form a substantially uniform arc and curvature with the front faces 156 of paddles 142 minimizing or preventing the formation of stress concentrations at the edges 160 of the paddle 142.

Experimental evidence indicates that the present retractor elements and assemblies described above substantially reduce body tissue trauma and minimize the damage to nerves which may cause paralysis. It appears that the recovery rate of patients enjoying the experimental use of the present invention is enhanced. Experimental evidence also shows that the present retractor elements and assemblies, compared to conventional instruments, greatly aid the surgeon in significantly decreasing the amount of time and the number of assistants required for surgery, particularly on very obese patients.

It should be understood that the above description is simply illustrative of the principles of this invention and that numerous other embodiments or modifications thereof may be devised that fall within the scope of the invention set forth by the following claims.

What is claimed is:

1. A surgical retractor assembly for holding a surgical incision open with body tissues held clear of a desired internal surgical area, comprising:

a retractor frame;

at least one resilient retractor paddle on the retractor frame adapted to extend from the frame into the incision;

said paddle including a paddle body having a front face adapted to engage the body tissues along the incision and an opposed back face adapted to face the desired surgical area;

said front and back faces extending laterally outward and downward from the frame to side and bottom edges; and wherein said paddle body is formed of a single soft non-metallic scissile material of sufficient resiliency with a flexural modulus of elasticity of between 1,000 psi and 75,000 psi throughout the cross section of the paddle body to allow the front face thereof to progressively bend resiliently from an original undeflected orientation into an arc transversely between the side edges in response to opposing forces applied to the paddle body as the retractor assembly is moved to open the incision, to thereby distribute applied forces over surfaces of the front face to minimize stress concentrations between the said paddle body and body tissues engaged thereby and to allow the body to return to its original orientation as the opposing forces are released as the front face of the paddle body is disengaged from the body tissues.

2. The surgical retractor assembly as claimed by claim 1 wherein said retractor frame is comprised of:
a paddle mounting arm having an upright section for mounting the paddle, and a horizontal section;
a pistol grip handle extending from the horizontal section of the paddle mounting arm, having a first handle section projecting angularly upward from the paddle mounting arm and a second handle section projecting angularly downward from the first handle section; and
a hand grip surface formed on one of the handle sections.

3. The surgical retractor assembly as claimed by claim 2 wherein the first and second handle sections are substantially perpendicular to one another.

4. The surgical retractor assembly as claimed by claim 2 wherein the first handle section extends at an obtuse angle from the horizontal section of the paddle mounting arm.

5. The surgical retractor assmebly as claimed by claim 2 wherein both handle sections include hand grip surfaces and further comprising a hand stop between the hand grip surfaces.

6. The surgical retractor assembly as claimed by claim 2 further comprising a hand stop at an outer end of the pistol grip handle projecting toward the paddle mounting arm.

7. The surgical retractor assembly as claimed by claim 2 further comprising vertical adjusting means interconnecting the paddle and paddle mounting arm for allowing vertical adjustment of the paddle along the upright section relative to the horizontal paddle section.

8. The surgical retractor assembly as claimed by claim 1 further comprising a ring member that is generally annular and is adapted to surround a major portion of an incision, and wherein the retractor frame includes a plurality of arm members, mounting a plurality of said retractor paddles at spaced locations to the ring member.

9. The surgical retractor assembly as claimed by claim 8 further comprising a releasable one-directional locking means operatively interconnecting the arm members and the ring member to enable the arms to be moved radially outward relative to the ring member to desired positions by applying radially outward force on the arm members and to prevent the arm members from moving radially inward to self-retain the arms in a desired radial position.

10. The surgical retractor assembly as claimed by claim 9 wherein the arm members are elongated and the releasable one-directional locking means includes a series of ratchet shoulder surfaces longitudinally spaced along the arm members and wherein the ring member has a plurality of angularly spaced pawls for releasably engaging the ratchet shoulder surfaces to retain the arm members at desired radial positions.

11. The surgical retractor assembly as claimed by claim 11 wherein the plurality of angularly spaced ratchet pawls are formed integrally with the ring member through flexible web sections to bias the pawls into engagement with the ratchet shoulder surfaces.

12. The surgical retractor assembly as claimed by claim 9 wherein the releasable one-directional locking means includes a plurality of ratchet pawls integrally formed with the ring member at fixed angularly spaced locations about the periphery of the ring member to accommodate a plurality of paddle arm members and to enable the arm members to be moved about the ring member.

13. The surgical retractor assembly as claimed by claim 12 wherein the ratchet pawls are sufficiently close to each other to allow an arm member to slide from one ratchet pawl to an adjacent ratchet pawl without releasing the arm member.

14. The surgical retractor assembly as claimed by claim 12 in which each ratchet pawl may be independently operated to release the arm member to enable the released arm member to be moved inward.

15. The surgical retractor assembly as claimed by claim 12 wherein each ratchet pawl is integrally formed with the ring member through an integrally interacting resilient web member.

16. The surgical retractor assembly as claimed by claim 8 wherein each arm member includes a horizontal section operatively connected to the frame and a vertical section that extends downward and angularly outward with respect to the horizontal section.

17. The surgical retractor assembly as claimed by claim 8 wherein the ring member includes an annular slot defined between two ring sections for receiving the arm members therein, in which the slot has a thickness between the two ring sections complementary to the arm members to slidably receive the arm members therein.

18. The surgical retractor assembly as claimed by claim 8 wherein the paddles include width dimensions sufficient to form a 360° barrier within the incision with the side edges of adjacent paddles overlapping.

19. The surgical retractor assembly as claimed by claim 8 wherein the paddles include diametrically opposed lateral paddles, diametrically opposed polar paddles and diametrically opposed lap paddles intermediate and overlapping the polar paddles and lateral paddles.

20. The surgical retractor assembly as claimed by claim 8 further comprising vertical adjustment means interconnecting the arm members and paddles for vertically adjusting the positions of the paddles with respect to the arm members.

21. The surgical retractor assemblies as claimed by claim 20 wherein the paddles each include upright slots for slidably receiving the arm members and wherein said adjustment means is comprised of detent projections along one of the arm members and detent recesses in the corresponding paddle interfitting with the one arm member to receive the detent projections thereon.

22. The surgical retractor assembly of claim 8 wherein at least two of the paddles overlap each other to cooperatively hold clear body tissues from the desired internal surgical area.

23. The surgical retractor assembly as claimed by claim 1 wherein the paddle has a non-uniform horizontal cross section with a decreasing thickness toward the side edges to enable adjacent paddles to be overlapped along their side edges to cooperatively hold clear body tissues from the desired internal surgical area.

24. The surgical retractor assembly as claimed by claim 1 wherein the paddle has a non-uniform vertical cross section with a decreasing thickness toward the bottom edge.

25. The surgical retractor assembly as claimed by claim 24 wherein the paddle is sufficiently resilient and the thickness adjacent the bottom edge is sufficiently thin to enable the bottom edge to be flexed more than 90° without breaking.

26. The surgical retractor assembly as claimed by claim 1 wherein the one soft scissile non-metallic paddle has an integral retaining projection vertically spaced below the frame that extends outward from the front face for extending radially outward beyond the incision under the body wall tissue to hold the retractor in place, said projection being formed of the same soft, scissile material as the paddle.

27. The surgical retractor assembly as claimed by claim 26 wherein the one paddle has a resilient, scissile skirt that extends downward below the retaining projection.

28. The surgical retractor assembly as claimed by claim 27 wherein the skirt has a vertical cross section that progessively decreases to a bottom edge providing a very flexible resilient bottom paddle periphery to minimize nerve damage.

29. The surgical retractor assembly as claimed by claim 1 wherein the paddle is formed of a soft, resilient scissile material having a flexural modulus of elasticity of between 2,000 psi and 20,000 psi.

30. The surgical retractor assembly as claimed in claim 1 wherein the paddle is formed of a meterial having a durometer hardness that is softer than D69 Shore and harder than A20 Shore.

31. The self-retaining surgical retractor as claimed by claim 1 wherein the paddle is formed of a scissile material having a durometer hardness that is softer than A99 Shore and harder than A60 Shore.

32. A surgical retractor paddle element mountable to a retractor frame for holding a surgical incision open with body tissues held clear of a desired surgical area, comprising:
    a paddle body of a single soft resilient scissile material having a front face and an opposed back face defined by opposed side edges, joined by extended opposed top and bottom edges;
    said paddle body having a flexural modulus of elasticity of between 1,000 psi and 75,000 psi throughout the cross section of the paddle body that is capable of flexing resiliently in an arc transversely between the side edges in response to opposing forces applied to the paddle body as the paddle element is moved to open the incision to thereby distribute applied forces over the front face to minimize stress concentrations between the paddle body and the engaged body tissues; and
    mounting means along one face thereof adapted to secure the paddle body to a retractor frame.

33. The surgical retractor paddle element as claimed by claim 32 wherein said body includes a non-uniform thickness dimension between said faces, said thickness dimension decreasing toward said peripheral sections.

34. The surgical retractor paddle as claimed by claim 32 wherein the paddle body further includes a skirt section along said bottom edge joining the peripheral sections, capable of flexing in an arc between said top and bottom edges.

35. The surgical retractor paddle as claimed by claim 34 wherein said body includes a nonuniform thickness dimension between said faces, said thickness dimension decreasing from a central section toward said skirt section.

36. The surgical retractor paddle as claimed in claim 32 wherein said paddle body includes an integral retaining projection that extends outward from the front face between the body edges.

37. The surgical retractor paddle as claimed by claim 32 wherein the paddle body is formed of a soft resilient flexible material having a flexural modulus of elasticity of between 2,000 psi and 20,000 psi.

38. The surgical retractor paddle as claimed by claim 32 wherein the paddle body is formed of a soft, scissile resilient material having a durometer hardness that is softer than D69 Shore and harder than A20 Shore.

39. The surgical retractor paddle as claimed by claim 32 wherein the paddle body is formed of a soft resilient material having a durometer hardness that is softer than A99 Shore and harder than A60 Shore.

40. A surgical retractor assembly for holding a surgical incision open with body tissues held clear of a desired internal surgical area, comprising:
    a ring member adapted to surround a major portion of the incision;
    a plurality of arm members adjustably mounted on the ring member;
    a plurality of retractor paddles mounted on the arm members adapted to extend into the incision;
    each of said paddles including a paddle body having a front face adapted to engage the body tissues along the incision and an opposed back face adapted to face the desired surgical area;
    said front and back faces extending laterally outward and downward from each arm member to side and bottom edges;
    a releasable one-directional ratchet and pawl locking means operatively interconnecting the arm member and the ring member to enable the arm members to be moved radially outward relative to the ring member to desired positions by applying outward radial force on the arm members and to prevent inadvertent inward radial movement of the arm members; and
    wherein said ratchet and pawl locking means include pawls that are formed integrally with the ring member and include a flexible web section that biases the pawls into engagement with ratchet teeth formed on the arm members.

41. The surgical retractor assembly of claim 40 wherein the ratchet teeth and pawls are curved complementary to the shape of the ring member to enable the arm members to slide angularly about the ring member with the teeth moving progressively from one pawl to an ajacent pawl.

* * * * *

UNITED STATES PATENT AND TRADEMARK OFFICE
CERTIFICATE OF CORRECTION

PATENT NO. : 4,421,107
DATED : December 20, 1983
INVENTOR(S) : Estes et al

It is certified that error appears in the above—identified patent and that said Letters Patent are hereby corrected as shown below:

The following individuals are listed as inventors (in addition to Roger Q. Estes and Jeffery S. Bjorkman-Estes):

John A. Moyer
E. 1825 - 36th Avenue
Spokane, WA 99203 and

Arthur J. Madsen
700 - 7th Avenue
Spokane, WA 99204

Signed and Sealed this

Nineteenth Day of June 1984

[SEAL]

Attest:

Attesting Officer

GERALD J. MOSSINGHOFF
Commissioner of Patents and Trademarks